(12) United States Patent
Torai et al.

(10) Patent No.: US 11,788,935 B2
(45) Date of Patent: Oct. 17, 2023

(54) SAMPLING DEVICE

(71) Applicants: NATIONAL UNIVERSITY CORPORATION KOBE UNIVERSITY, Kobe (JP); SHIMADZU CORPORATION, Kyoto (JP)

(72) Inventors: Aya Torai, Kyoto (JP); Yoshihiro Matsumoto, Kyoto (JP); Tomohisa Hasunuma, Kobe (JP)

(73) Assignees: NATIONAL UNIVERSITY CORPORATION KOBE UNIVERSITY, Kobe (JP); SHIMADZU CORPORATION, Kyoto (JP)

( * ) Notice: Subject to any disclaimer, the term of this patent is extended or adjusted under 35 U.S.C. 154(b) by 219 days.

(21) Appl. No.: 17/259,602

(22) PCT Filed: Jul. 10, 2019

(86) PCT No.: PCT/JP2019/027323
§ 371 (c)(1),
(2) Date: Feb. 16, 2022

(87) PCT Pub. No.: WO2020/017407
PCT Pub. Date: Jan. 23, 2020

(65) Prior Publication Data
US 2022/0221378 A1    Jul. 14, 2022

(30) Foreign Application Priority Data
Jul. 17, 2018   (JP) ................................ 2018-134169

(51) Int. Cl.
*G01N 30/38*   (2006.01)
*G01N 1/20*    (2006.01)
(Continued)

(52) U.S. Cl.
CPC .......... *G01N 1/2035* (2013.01); *G01N 30/38* (2013.01); *G01N 30/7233* (2013.01); *G01N 2030/027* (2013.01)

(58) Field of Classification Search
CPC .. G01N 1/2035; G01N 30/38; G01N 30/7233; G01N 2030/027; G01N 30/72;
(Continued)

(56) References Cited

U.S. PATENT DOCUMENTS 3,282,113 A  *  11/1966  Sachnik ................. F16L 55/00
                                              73/863.02
4,022,066 A  *   5/1977  Kaune ................. G01N 1/2035
                                              73/863.86
(Continued)

FOREIGN PATENT DOCUMENTS

JP        04-269641 A      9/1992
JP        8-35958    †    2/1996
(Continued)

OTHER PUBLICATIONS

Office Action dated Feb. 15, 2022 in Japanese Application No. 2020-531262.
(Continued)

*Primary Examiner* — David J Bolduc
(74) *Attorney, Agent, or Firm* — Sughrue Mion, PLLC

(57) ABSTRACT

A sampling apparatus 1 samples a culture medium in a bioreactor 11. A pump 21 circulates the culture medium in the bioreactor 11 via a flow path 41 by leading out the culture medium from the bioreactor 11 into the flow path 41 and introducing the culture medium from the flow path 41 into the bioreactor 11. A valve 22 is provided in the middle of the flow path 41, and switches a flow path such that the culture medium circulated in the flow path 41 flows out to a branch flow path 42 to be sampled.

4 Claims, 10 Drawing Sheets

(51) Int. Cl.
*G01N 30/72* (2006.01)
*G01N 30/02* (2006.01)

(58) Field of Classification Search
CPC ....... G01N 2030/201; G01N 2030/202; G01N 30/20; C12M 33/00
See application file for complete search history.

(56) References Cited

U.S. PATENT DOCUMENTS

| | | | | |
|---|---|---|---|---|
| 4,352,780 | A * | 10/1982 | Schick | G01N 35/1097 422/68.1 |
| 5,480,614 | A * | 1/1996 | Kamahori | B01L 3/50273 422/50 |
| 6,718,817 | B1 * | 4/2004 | Ko | G01N 30/20 73/863.71 |
| 10,138,456 | B2 * | 11/2018 | Shimase | C12M 29/18 |
| 2004/0259189 | A1 * | 12/2004 | Marschke | G01N 35/02 435/34 |
| 2012/0252110 | A1 | 10/2012 | Oura et al. | |
| 2013/0143307 | A1 | 6/2013 | Nozaki et al. | |
| 2016/0299168 | A1 | 10/2016 | Tsukada et al. | |
| 2017/0191019 | A1 * | 7/2017 | Kawarai | C12M 41/00 |
| 2018/0258377 | A1 * | 9/2018 | Shimase | F16K 7/06 |
| 2018/0371399 | A1 * | 12/2018 | Griffin | C12M 29/14 |
| 2019/0368980 | A1 * | 12/2019 | Barmash | G01N 1/2035 |
| 2020/0181555 | A1 * | 6/2020 | Hinojosa | C12M 29/10 |

FOREIGN PATENT DOCUMENTS

| | | |
|---|---|---|
| JP | 10-19743 A | 1/1998 |
| JP | 2004-357575 A | 12/2004 |
| JP | 2011-103882 A | 6/2011 |
| JP | 2012-200239 A | 10/2012 |
| JP | 2016-537001 A | 12/2016 |
| WO | 2012/020458 A1 | 2/2012 |
| WO | 2015/073913 A1 | 5/2015 |
| WO | 2015/079534 A1 | 6/2015 |

OTHER PUBLICATIONS

International Search Report of PCT/JP2019/027323 dated Oct. 8, 2019 [PCT/ISA/210].
Written Opinion of PCT/JP2019/027323 dated Oct. 8, 2019 [PCT/ISA/237].

\* cited by examiner
† cited by third party

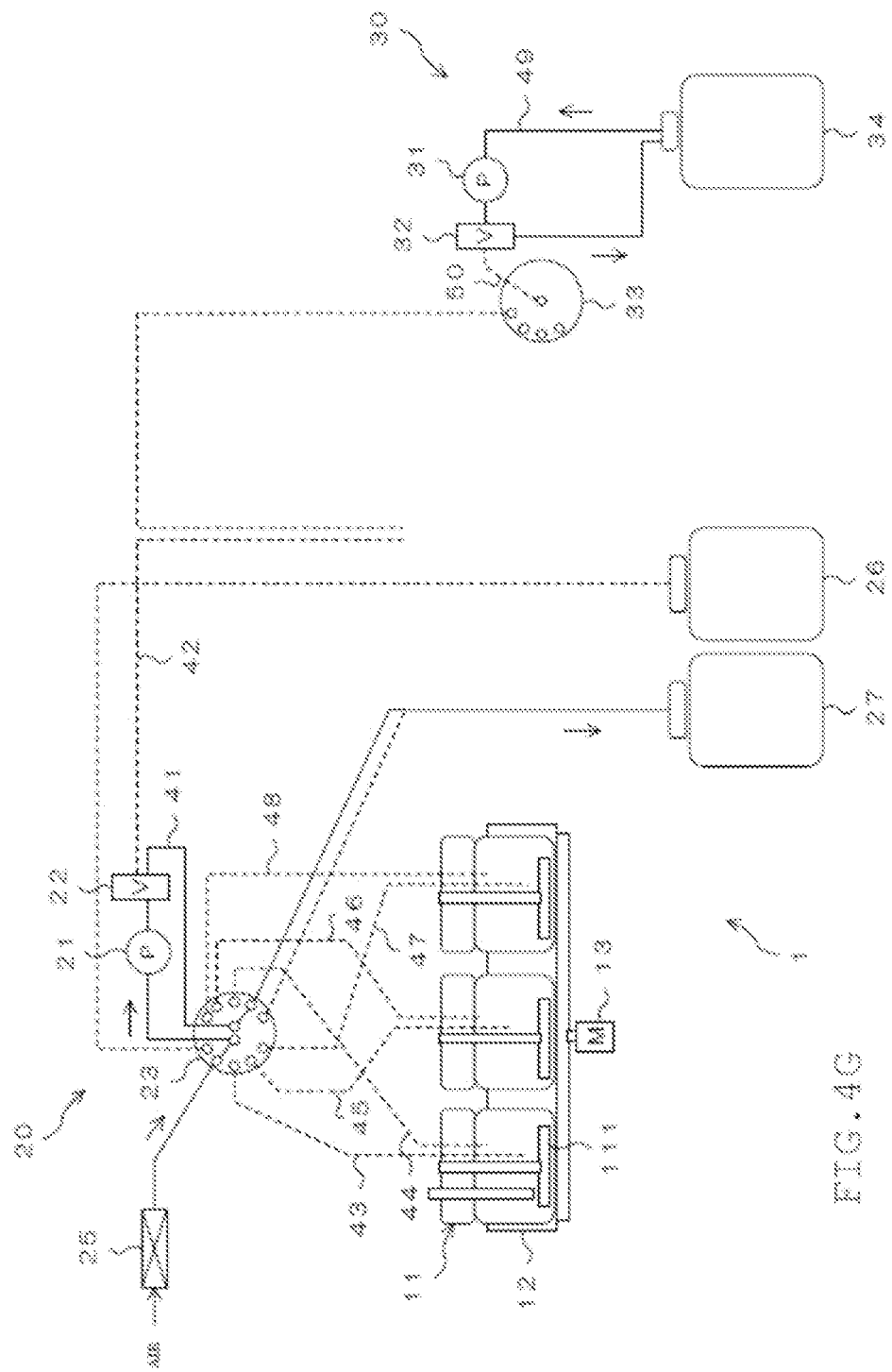

SAMPLING DEVICE

CROSS REFERENCE TO RELATED APPLICATIONS

This application is a National Stage of International Application No. PCT/JP2019/027323 filed Jul. 10, 2019, claiming priority based on Japanese Patent Application No. 2018-134169 filed Jul. 17, 2018.

TECHNICAL FIELD

The present invention relates to a sampling apparatus for sampling a liquid in a container.

BACKGROUND ART

A technology has been known in which an analysis such as metabolome analysis is performed by culturing cells of microorganisms and plants in a culture medium in a culture vessel, collecting cells from the culture medium, performing pre-processing, and then supplying the cells to a liquid chromatograph mass spectrometer. In this kind of technology, a sampling apparatus for sampling a culture medium containing cells and a pre-processing apparatus for performing pre-processing on the cells contained in the sampled culture medium are used. The sampling of the culture medium is performed under an aseptic condition (refer to, for example, Patent Document 1 below).

As a method of sampling the culture medium, a method of feeding the culture medium to a flow path connected to the culture vessel using a liquid feeder, a method of inserting a needle into the culture vessel and sucking a required amount of the culture medium, and the like have been known. In the method of feeding the culture medium in the culture vessel to the flow path by using the liquid feeder, the culture medium is not exposed to the outside air, so that sampling can be performed while keeping the culture medium under an aseptic condition. On the other hand, in the method of inserting the needle into the culture vessel and sucking the culture medium, the needle is inserted into the culture vessel after a lid of the culture vessel is removed. Therefore, the culture medium in the culture vessel is exposed to the outside air, so that it is necessary to perform the sampling in a sterile room.

PRIOR ART DOCUMENT

Patent Document

Patent Document 1: Japanese Patent Laid-Open No. 2012-200239

SUMMARY OF THE INVENTION

Problems to be Solved by the Invention

In the method of feeding the culture medium in the culture vessel to the flow path by using the liquid feeder, for example, a tubing pump is used as the liquid feeder. This type of liquid feeder can feed the liquid with a simple configuration by deforming (compressing and relaxing) a flexible tube, but there is a problem that it is difficult to sample the culture medium in an accurate amount.

On the other hand, in the method of inserting the needle into the culture vessel and sucking the culture medium, it is possible to perform the sampling by sucking the culture medium into the needle in an accurate amount. However, since it is necessary to provide a sterile room, there is a problem that the equipment becomes large and the configuration for operating the needle becomes complicated.

The above-described problems may occur not only in a case of sampling the culture medium but also in a case of sampling various liquids other than the culture medium from the inside of the container.

The invention has been made in view of the above circumstances, and an object of the invention is to provide a sampling apparatus capable of sampling an accurate amount of liquid with a simple configuration.

Means for Solving the Problems (1) A sampling apparatus according to the invention is a sampling apparatus that samples a liquid in a container, and includes a circulation mechanism and a flow path switching unit. The circulation mechanism circulates the liquid in the container via a circulation flow path by leading out the liquid from the container into the circulation flow path and introducing the liquid from the circulation flow path into the container. The flow path switching unit is provided in the middle of the circulation flow path, and switches a flow path such that the liquid circulated in the circulation flow path flows out to a branch flow path to be sampled.

According to such a configuration, with a simple configuration in which the flow path is only switched by using the flow path switching unit while the liquid in the container is circulated in the circulation flow path, sampling can be performed by causing the liquid circulated in the circulation flow path to flow out to the branch flow path. When the flow path is switched by the flow path switching unit for a predetermined time in a state where the liquid is stably circulated in the circulation flow path, an accurate amount of liquid according to the time can be sampled. In addition, sampling can be performed at high speed by repeating the switching of the flow path by the flow path switching unit in a short time.

(2) The circulation mechanism may have a flexible tube constituting at least a part of the circulation flow path. In this case, the circulation mechanism may feed the liquid in the tube by deforming the tube.

According to such a configuration, the sampling of the liquid can be performed by using a simple configuration in which the flexible tube is deformed to feed the liquid. Further, when the inside of the tube becomes dirty or the like, maintenance can be performed easily and inexpensively simply by replacing the tube.

(3) The sampling apparatus may further include a control unit. The control unit controls a sampling amount of the liquid by controlling time for switching the flow path by the flow path switching unit.

According to such a configuration, the sampling amount of the liquid can be accurately controlled by accurately controlling the time for switching the flow path by the flow path switching unit, using the control unit.

(4) The control unit may collect the liquid into the container by causing the liquid in the circulation flow path to flow back after the liquid is sampled.

According to such a configuration, the liquid remaining in the circulation flow path can be collected into the container by causing the liquid in the circulation flow path to flow back after the liquid is sampled. Therefore, the amount of the liquid used in the container can be suppressed as compared with a case where the liquid remaining in the circulation flow path is drained as it is.

(5) The control unit may introduce a cleaning liquid into at least a part of the circulation flow path and drain the cleaning liquid after the liquid in the circulation flow path is collected into the container.

According to such a configuration, the liquid remaining in the circulation flow path is collected into the container after the liquid is sampled, and then the inside of the circulation flow path can be cleaned with the cleaning liquid. As a result, it is possible to reliably prevent the next sampling from being performed with the liquid remaining in the circulation flow path.

(6) The liquid in the container may be a culture medium containing cells.

According to such a configuration, it is possible to sample an accurate amount of culture medium with a simple configuration when sampling the culture medium containing cells.

Effects of the Invention

According to the invention, when the flow path is switched by the flow path switching unit for a predetermined time in a state where the liquid is stably circulated in the circulation flow path with a simple configuration in which the flow path is only switched by using the flow path switching unit while the liquid in the container is circulated in the circulation flow path, an accurate amount of liquid according to the time can be sampled.

BRIEF DESCRIPTION OF THE DRAWINGS

FIG. 4G is a flow path diagram for describing the operation of the sampling apparatus.

MODE FOR CARRYING OUT THE INVENTION

1. Schematic Configuration of Automatic Pre-Processing System

Figure 1:
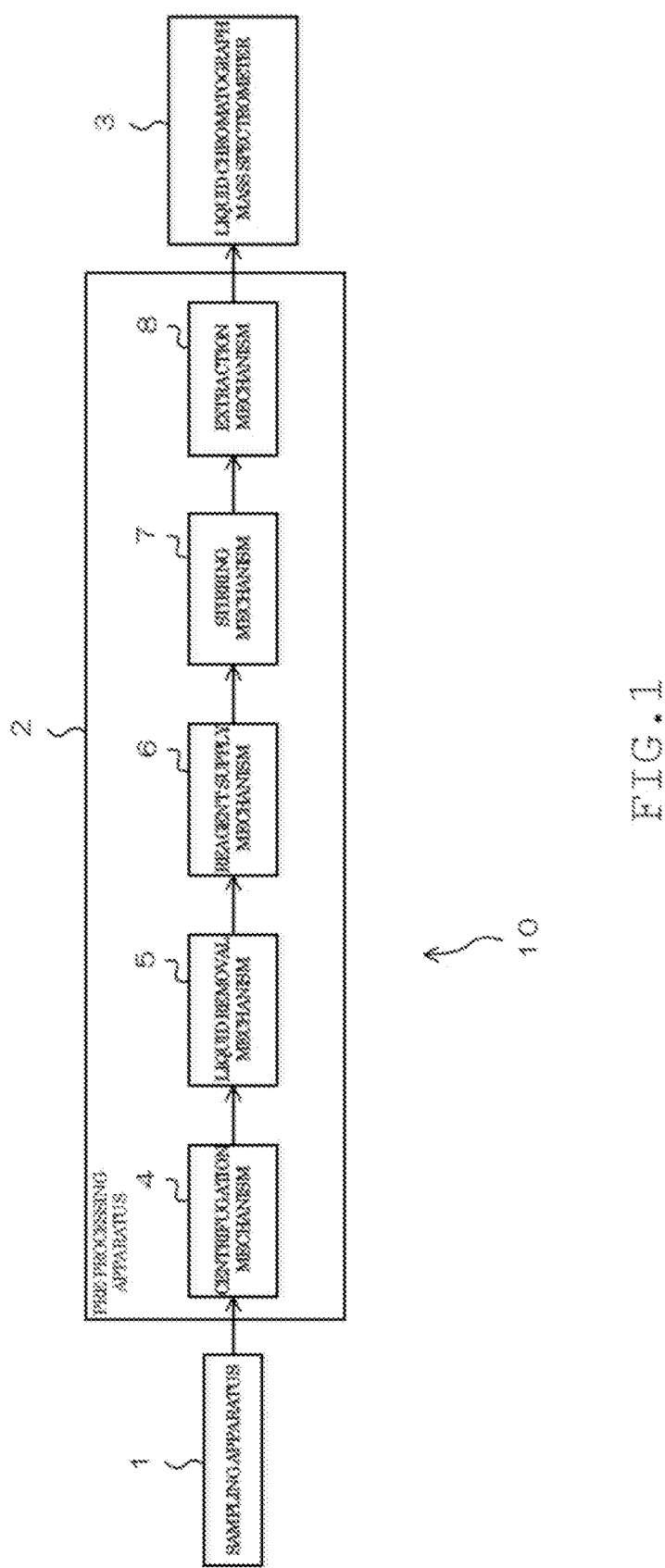
FIG. 1 is a block diagram illustrating a schematic configuration of an automatic pre-processing system including a sampling apparatus according to an embodiment of the invention.

FIG. 1 is a block diagram illustrating a schematic configuration of an automatic pre-processing system 10 including a sampling apparatus 1 according to an embodiment of the invention. The automatic pre-processing system 10 is a device for automatically performing pre-processing on an analysis target. In the present embodiment, the analysis target is, for example, a cultured cell, and more specifically, a bacterial cell.

The automatic pre-processing system 10 includes the sampling apparatus 1 and a pre-processing apparatus 2. The metabolites of the cells are extracted from the cells after the pre-processing is performed by the automatic pre-processing system 10, and are supplied to a liquid chromatograph mass spectrometer 3. The liquid chromatograph mass spectrometer 3 is only an example of an analysis device for analyzing an analysis target, and it is also possible to perform an analysis by using another analysis device.

The sampling apparatus 1 is a apparatus for sampling a liquid from a container (culture container). For example, the cells of microorganisms and plants are cultured in a culture medium in a container called a bioreactor, and the culture medium containing the cells in the bioreactor is sampled by the sampling apparatus 1. In the bioreactor, for example, a stirring member that is rotated by using magnetic force, an oxygen concentration sensor for detecting the concentration of dissolved oxygen, and the like are provided, and the cells are cultured in the sampling apparatus 1 by adjusting the dissolved oxygen concentration while stirring the culture medium in the bioreactor.

The pre-processing apparatus 2 performs pre-processing on the cells contained in the culture medium sampled from the bioreactor. In the sampling apparatus 1, the culture medium containing the cells is housed in a test tube as a container (sampling container). The pre-processing apparatus 2 is provided with a centrifugation mechanism 4, a liquid removal mechanism 5, a reagent supply mechanism 6, a stirring mechanism 7, an extraction mechanism 8, and the like, and by each of these mechanisms, the pre-processing is sequentially performed on the cells contained in the culture medium in the test tube.

The centrifugation mechanism 4 centrifuges the test tube in which the culture medium containing the cells is housed. As a result, centrifugal force is applied to the culture medium in the test tube, and the cells (solid) and the liquid other than the cells are separated. Then, the liquid other than the cells centrifuged in the test tube by the centrifugation mechanism 4 is removed by using the liquid removal mechanism 5, and thereby the cells are collected.

The reagent is supplied by the reagent supply mechanism 6, to the test tube after the liquid is removed by the liquid removal mechanism 5. As a result, the reagent is mixed with the cells in the test tube, and a mixed solution is generated. Then, the mixed solution generated by the reagent supply mechanism 6 is stirred by the stirring mechanism 7.

The reagent used in the present embodiment is a reagent for extracting metabolites in the cells, and a suspension in which the metabolites are extracted from the cells is obtained by stirring the mixed solution in which the reagent is mixed with the cells. Apart of the suspension obtained in this manner is extracted as an extraction liquid by the extraction mechanism 8, and is supplied to the liquid chromatograph mass spectrometer 3.

2. Flow Path Configuration of Sampling Apparatus

Figure 2:
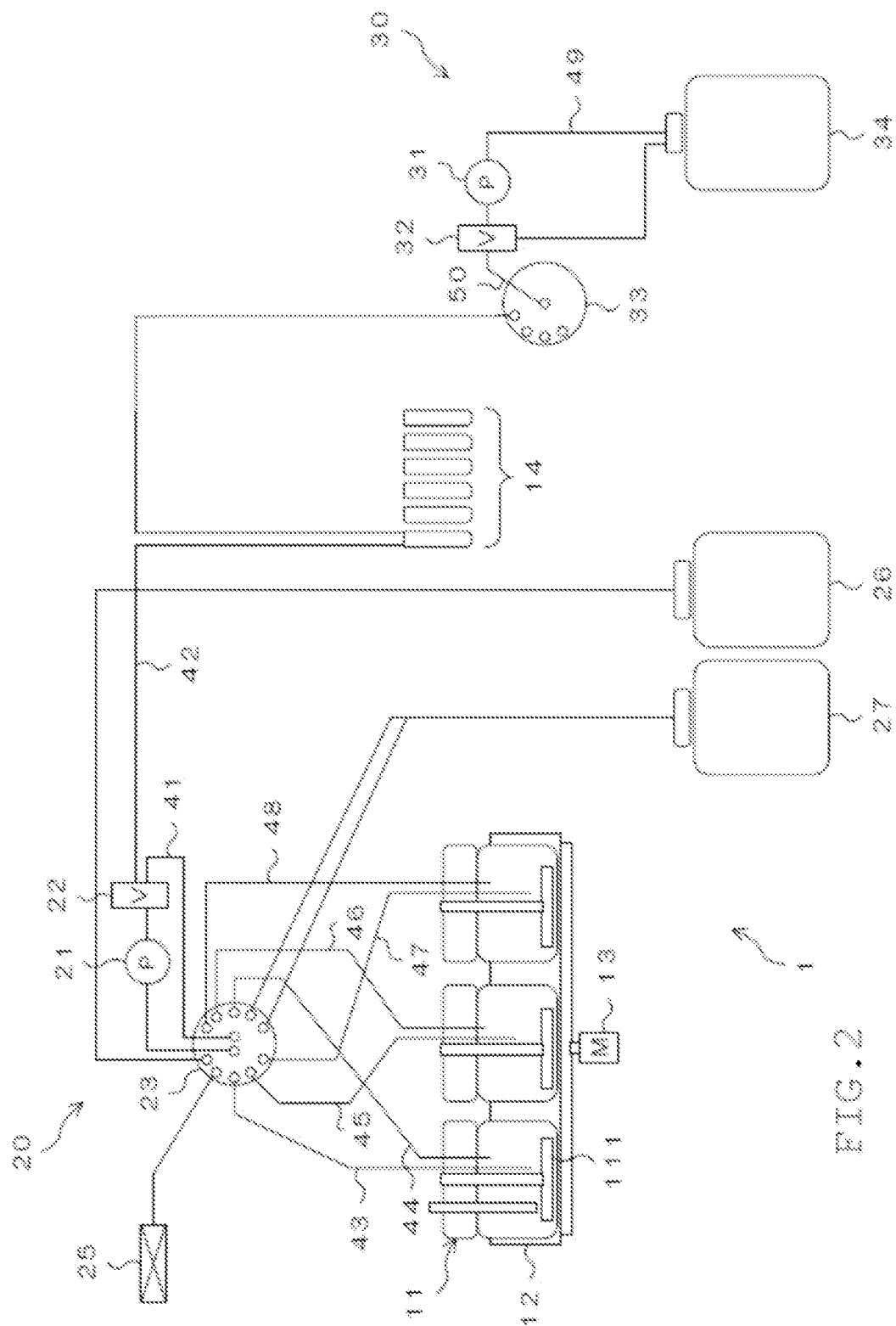
FIG. 2 is a flow path diagram illustrating a flow path configuration of the sampling apparatus.

FIG. 2 is a flow path diagram illustrating a flow path configuration of the sampling apparatus 1. In the sampling apparatus 1, the culture medium containing the cells in the bioreactor 11 is sampled. A stirring member 111 that is rotated by using magnetic force is provided in the bioreactor 11.

The bioreactor 11 is held by a holding unit 12 provided in the sampling apparatus 1. In the present embodiment, one holding unit 12 can hold three bioreactors 11, and a plurality of such holding units 12 are provided. However, a configuration in which one holding unit 12 is provided may be adopted, or a configuration in which one holding unit 12 can hold two or less or four or more bioreactors 11 may be adopted.

The bioreactor 11 can carry out the culture in a state of being heated by a heater (not illustrated) provided in the holding unit 12. Further, a motor 13 for rotating a magnet (not illustrated) is connected to the holding unit 12. The magnet is rotated by rotating the motor 13, and the stirring member 111 in each bioreactor 11 can be rotated by the magnetic force thereof.

In the present embodiment, the culture medium can be stirred by the stirring member 111 to carry out the culture while controlling the temperature of the culture medium in the bioreactor 11. Then, in the sampling apparatus 1, the culture medium containing the cultured cells can be sampled in a test tube 14 at an arbitrary timing.

The sampling apparatus 1 is provided with a culture medium sampling mechanism 20 for sampling the culture medium in the test tube 14, and a reagent sampling mechanism 30 for sampling the reagent in the test tube 14. The test tube 14 houses the mixed solution in which the culture medium and the reagent are mixed with each other, is sealed by a cap (not illustrated), and is transferred to the pre-processing apparatus 2.

The culture medium sampling mechanism 20 includes a pump 21 and a plurality of valves 22 and 23. The valve 23 has, for example, one pair of common ports and five pairs of selection ports (10 selection ports in total), and any one pair of selection ports is arbitrarily selected to be connected to the one pair of common ports, so that the flow path can be switched.

The pump 21 and the valve 22 are provided in a flow path 41 connecting the one pair of common ports. The valve 22 constitutes a flow path switching unit (first flow path switching unit) for switching whether or not to guide the liquid in the flow path 41 to a branch flow path 42 that branches with respect to the flow path 41. That is, the valve 22 can switch between a state in which the liquid flows between the one pair of common ports via the flow path 41 and a state in which the liquid in the flow path 41 is guided to the branch flow path 42.

Among the five pairs of selection ports, one pair of selection ports is connected to a lead-out path 43 and an introduction path 44 that communicate with one bioreactor 11, respectively. The lead-out path 43 is a flow path for leading out the culture medium in the bioreactor 11. On the other hand, the introduction path 44 is a flow path for introducing the culture medium, which has been led out from the bioreactor 11 via the lead-out path 43 and has been circulated through the flow path 41, into the bioreactor 11 again. Further, another pair of selection ports is connected to a lead-out path 45 and an introduction path 46 that communicate with another bioreactor 11, respectively. Still another pair of selection ports is connected to a lead-out path 47 and an introduction path 48 that communicate with still another bioreactor 11.

In the present embodiment, one of the lead-out paths 43, 45, and 47 and the corresponding one of the introduction paths 44, 46, and 48 are caused to communicate with each other via the flow path 41, and the pump 21 is driven in that state, so that the culture medium in each bioreactor 11 can be circulated. That is, the flow path 41, each of the lead-out paths 43, 45, and 47, and each of the introduction paths 44, 46, and 48 constitute a circulation flow path (first circulation flow path) for circulating the culture medium in each bioreactor 11. The pump 21 constitutes a circulation mechanism (first circulation mechanism) for circulating the culture medium in each bioreactor 11 via the first circulation flow path by leading out the culture medium from each bioreactor 11 into the first circulation flow path and also introducing the culture medium into each bioreactor 11 from the first circulation flow path.

The tip end of each of the lead-out paths 43, 45, and 47 is immersed in the culture medium in the corresponding bioreactor 11. On the other hand, the tip end of each of the introduction paths 44, 46, and 48 is located at a position separated upward from the culture medium in the corresponding bioreactor 11. Therefore, the culture medium that is led out from the bioreactor 11 via each of the lead-out paths 43, 45, and 47 and is circulated through the flow path 41 falls from the tip end of each of the introduction paths 44, 46, and 48 to be introduced into the bioreactor 11.

In the present embodiment, in the flow path 41 connecting the one pair of common ports, at least a portion where the pump 21 is provided is composed of a flexible tube. The pump 21 is, for example, a tubing pump, and can feed the liquid in the flexible tube by deforming (compressing and relaxing) the tube.

When the valve 22 as the first flow path switching unit provided in the middle of the flow path 41 is switched, the culture medium circulated in each bioreactor 11 via the flow path 41 can flow out to the branch flow path 42. At this time, the tip end of the branch flow path 42 is arranged in the test tube 14, and the culture medium is sampled in the test tube 14 via the branch flow path 42.

Of the two pairs of selection ports other than the three pairs of selection ports to which the lead-out paths 43, 45, and 47 and the introduction paths 44, 46, and 48 are connected, one pair of selection ports is connected to a cleaning liquid tank 26 and a waste liquid tank 27. Further, the remaining one pair of selection ports is connected to a filter 25 and the waste liquid tank 27, respectively. A cleaning liquid for cleaning the flow path for the culture medium is housed in the cleaning liquid tank 26.

After the culture medium is sampled in the test tube 14 from any of the bioreactors 11, when the valve 23 is switched to connect the cleaning liquid tank 26 and the waste liquid tank 27 to the flow path 41 and the pump 21 is driven in that state, the cleaning liquid in the cleaning liquid tank 26 is drained into the waste liquid tank 27 via the flow path 41. As a result, the flow path 41, the valve 22 provided in the flow path 41, and the like can be cleaned with the cleaning liquid.

Further, after the cleaning with the cleaning liquid, when the valve 23 is switched to connect the filter 25 and the waste liquid tank 27 to the flow path 41 and the pump 21 is driven in that state, air is introduced into the flow path 41 through the filter 25, and is discharged into the waste liquid tank 27 together with the water remaining in the flow path 41. As a result, water can be removed from the flow path 41, the valve 22 provided in the flow path 41, and the like.

The reagent sampling mechanism 30 includes a pump 31 and a plurality of valves 32 and 33. The valve 33 has, for example, one common port and a plurality of selection ports, and any one of the selection ports is arbitrarily selected to be connected to the common port, so that the flow path can be switched.

The pump 31 and the valve 32 are provided in a flow path 49 of which both ends communicate with a reagent tank 34. A reagent to be mixed with the sampled culture medium in the test tube 14 is housed in the reagent tank 34. The flow path 49 constitutes a circulation flow path (second circulation flow path) for circulating the reagent in the reagent tank 34. The pump 31 constitutes a circulation mechanism (second circulation mechanism) for circulating the reagent in the reagent tank 34 via the second circulation flow path by leading out the reagent from the reagent tank 34 into the second circulation flow path and also introducing the reagent into the reagent tank 34 from the second circulation flow path.

In the present embodiment, in the flow path 49 of which the both ends are connected to the reagent tank 34, at least a portion where the pump 31 is provided is composed of a flexible tube. The pump 31 is, for example, a tubing pump, and can feed the reagent in the flexible tube by deforming (compressing and relaxing) the tube.

The valve 32 constitutes a flow path switching unit (second flow path switching unit) for switching whether or not to guide the liquid in the flow path 49 to a branch flow path 50 that branches with respect to the flow path 49. That is, the valve 32 can switch between a state in which the reagent in the reagent tank 34 is circulated via the flow path 49 and a state in which the reagent in the flow path 49 is guided to the branch flow path 50.

In this way, when the valve 32 as the second flow path switching unit provided in the middle of the flow path 49 is switched, the reagent circulated in the reagent tank 34 via the flow path 49 can flow out to the branch flow path 50. The branch flow path 50 is connected to the common port of the valve 33, and one of the selection ports of the valve 33 is connected to the inside of the test tube 14. Therefore, when the selection port connected to the inside of the test tube 14 is caused to communicate with the common port, the reagent flowing out from the flow path 49 to the branch flow path 50 can be sampled in the test tube 14.

3. Electrical Configuration of Sampling Apparatus

Figure 3:
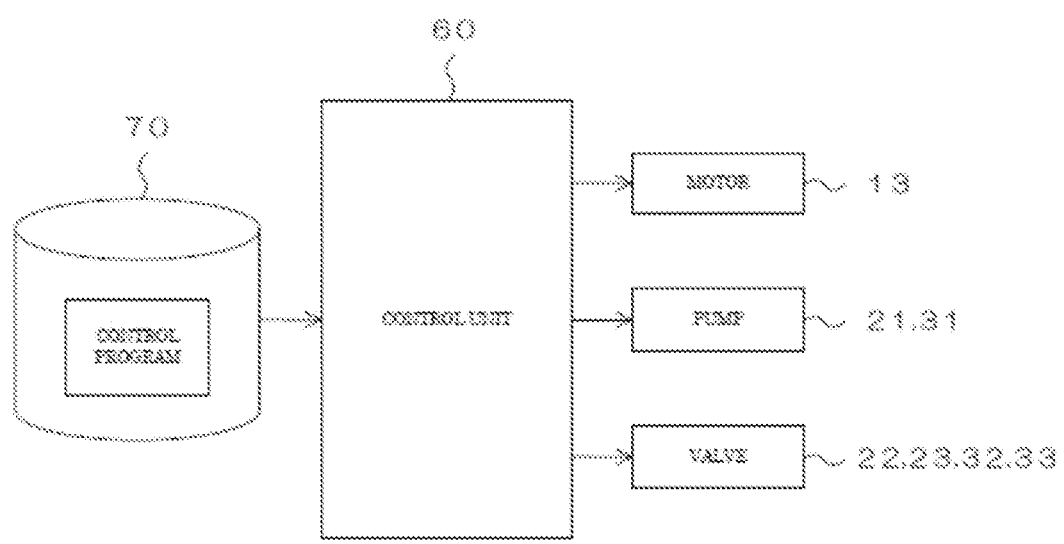
FIG. 3 is a block diagram illustrating an electrical configuration of the sampling apparatus.

FIG. 3 is a block diagram illustrating an electrical configuration of the sampling apparatus 1. The sampling apparatus 1 includes a control unit 60, a storage unit 70, and the like in addition to the motor 13, the pumps 21 and 31, and the valves 22, 23, 32, and 33 described above.

The control unit 60 includes, for example, a central processing unit (CPU), and the CPU executes a control program to control the operation of the motor 13, the pumps 21 and 31, the valves 22, 23, 32, and 33, and the like. The storage unit 70 is composed of, for example, a read only memory (ROM) and a random access memory (RAM), and can store various kinds of data in addition to the above-described control program.

The control unit 60 can circulate the culture medium in any of the bioreactors 11 by driving the pump 21 at a constant liquid feeding speed in a state where one of the lead-out paths 43, 45, and 47 and the corresponding one of the introduction paths 44, 46, and 48 communicate with each other via the flow path 41. The control unit 60 samples the culture medium in the flow path 41, in the test tube 14 by switching the valve 22 for a predetermined time based on the control program to cause the flow path 41 to communicate with the branch flow path 42.

At this time, the control unit 60 can control the sampling amount of the culture medium by controlling the time for switching the flow path by the valve 22. That is, when the liquid feeding speed of the pump 21 is known in advance, a desired amount of culture medium can be accurately sampled in the test tube 14 by adjusting the time for which the flow path 41 communicates with the branch flow path 42.

The control unit 60 can circulate the reagent in the reagent tank 34 by driving the pump 31 at a constant liquid feeding speed in a state where one end of the flow path 49 communicates with the other end thereof. The control unit 60 samples the reagent in the flow path 49 in the test tube 14 by switching the valve 32 for a predetermined time based on the control program to cause the flow path 49 to communicate with the branch flow path 50 and switching the valve 33 to cause the branch flow path 50 to communicate with the test tube 14.

At this time, the control unit 60 can control the sampling amount of the reagent by controlling the time for switching the flow path by the valve 32. That is, when the liquid feeding speed of the pump 31 is known in advance, a desired amount of reagent can be accurately sampled in the test tube 14 by adjusting the time for which the flow path 49 communicates with the branch flow path 50.

4. Operation of Sampling Apparatus

FIGS. 4A to 4G are flow path diagrams for describing the operation of the sampling apparatus 1. In FIGS. 4A to 4G, the flow path illustrated by the solid line illustrates a state in which liquid (culture medium, cleaning liquid, or reagent), gas (air), or the like is flowing, and the flow path illustrated by the broken line illustrates a state in which liquid or gas is not flowing.

Figure 4A:
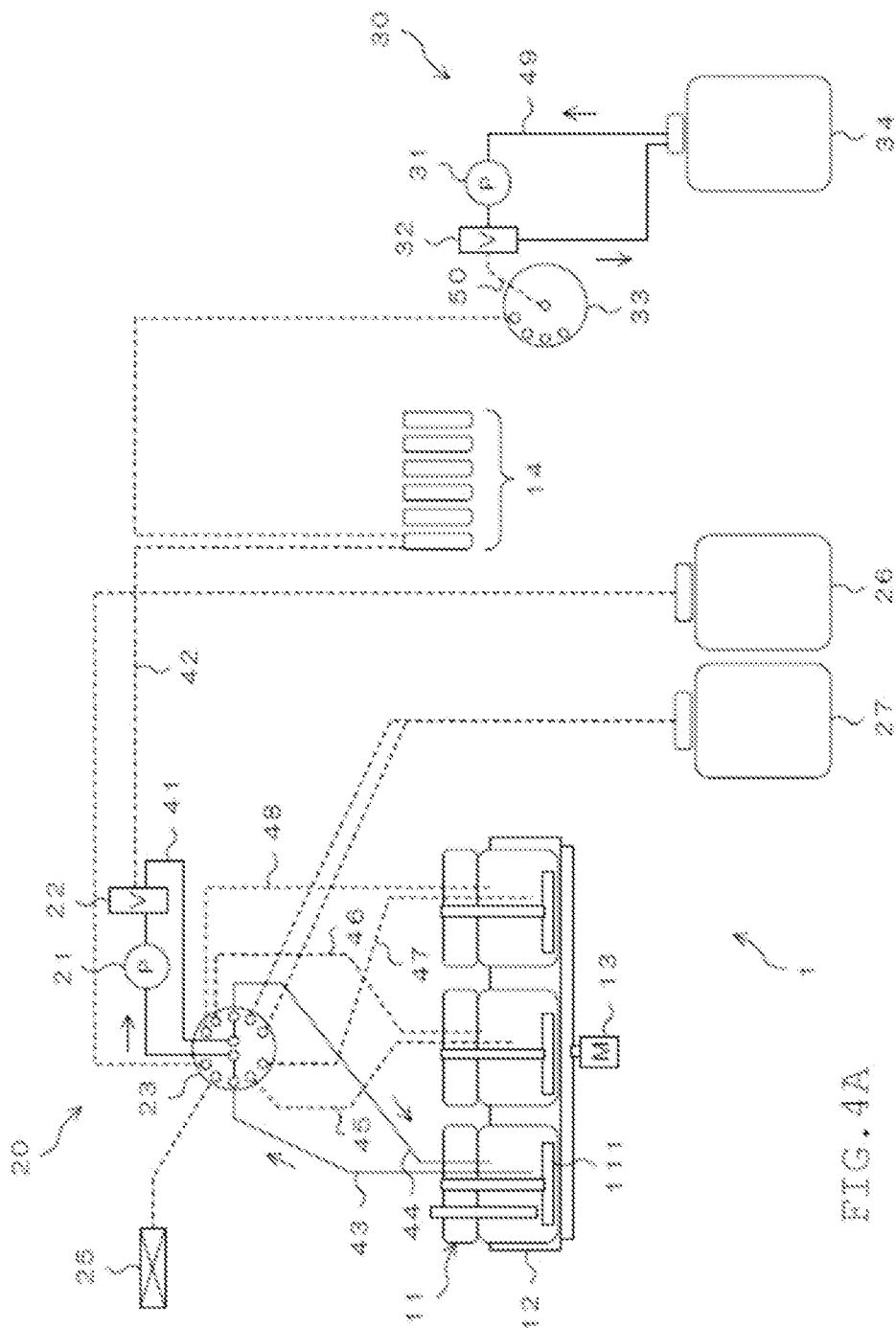
FIG. 4A is a flow path diagram for describing an operation of the sampling apparatus.

In the state illustrated in FIG. 4A, the lead-out path 43 and the introduction path 44 that communicate with one bioreactor 11 communicate with each other via the flow path 41. By driving the pump 21 in this state, the culture medium in the bioreactor 11 is circulated. At this time, one end of the flow path 49 for the reagent communicates with the other end thereof, and the pump 31 is driven, so that the reagent in the reagent tank 34 is circulated.

Figure 4B:
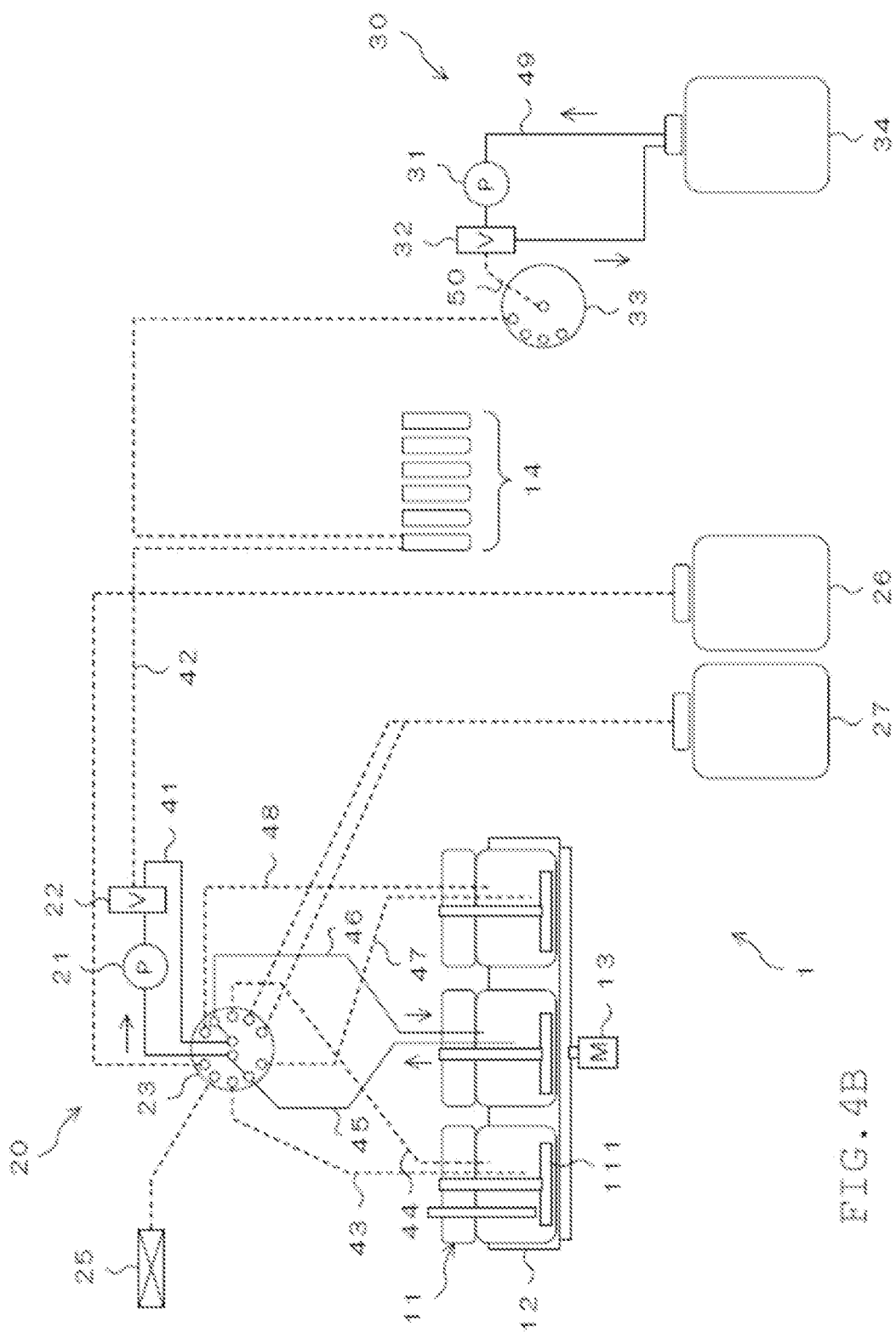
FIG. 4B is a flow path diagram for describing the operation of the sampling apparatus.

In a case where the valve 23 is switched as illustrated in FIG. 4B, the lead-out path 45 and the introduction path 46 that communicate with another bioreactor 11 communicate with each other via the flow path 41, and the pump 21 is driven in this state to circulate the culture medium in the corresponding bioreactor 11. In a case where the valve 23 is switched as illustrated in FIG. 4C, the lead-out path 47 and the introduction path 48 that communicate with still another bioreactor 11 communicate with each other via the flow path 41, and the pump 21 is driven in this state to circulate the culture medium in the corresponding bioreactor 11.

Figure 4C:
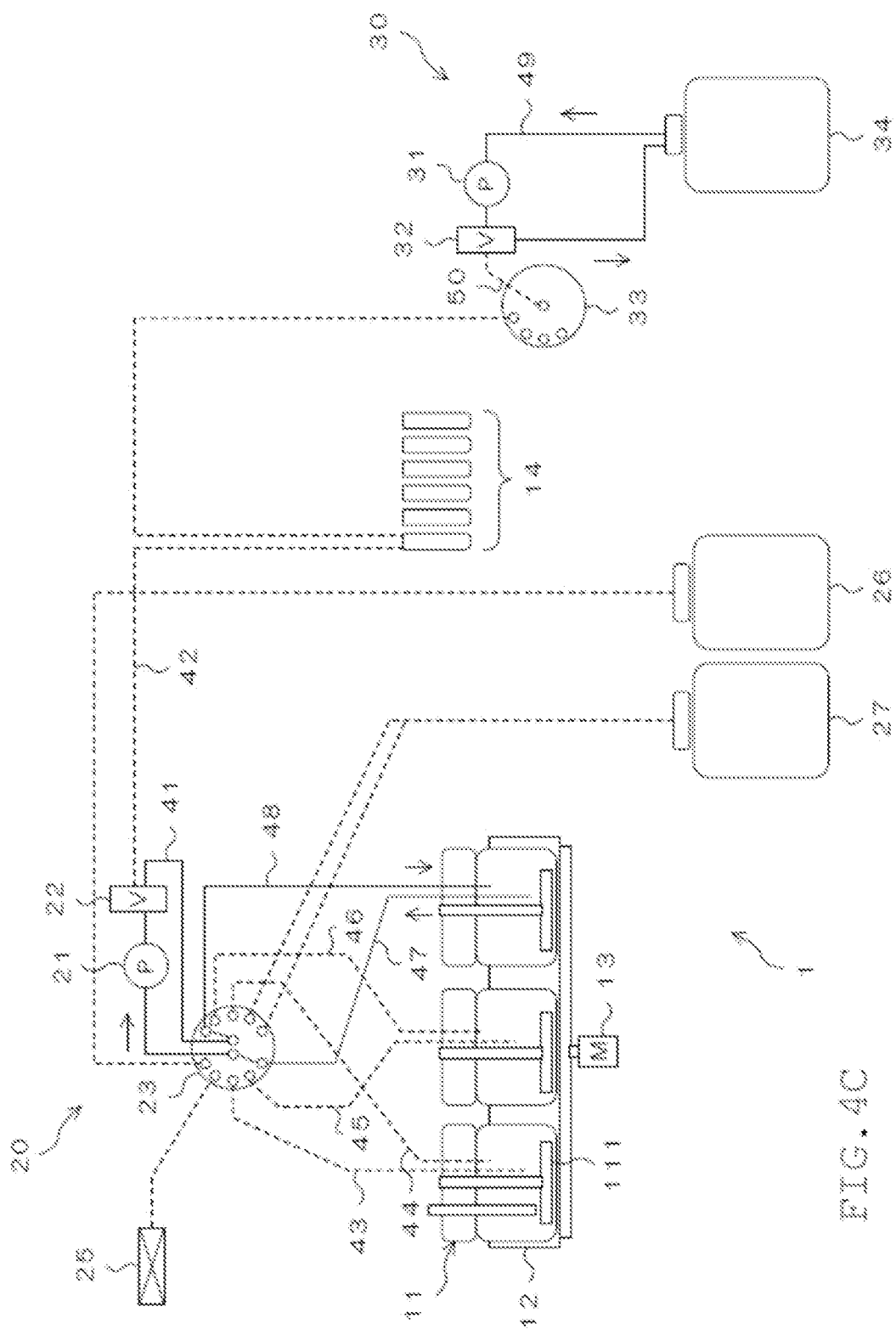
FIG. 4C is a flow path diagram for describing the operation of the sampling apparatus.

When the valve 22 is switched from any of the states illustrated in FIGS. 4A to 4C to connect the flow path 41 and the branch flow path 42, the culture medium circulated in the flow path 41 flows out to the branch flow path 42 to be sampled in the test tube 14. For example, as illustrated in FIG. 4D, when the valve 22 is switched from the state illustrated in FIG. 4A, the culture medium circulated through the lead-out path 43, the flow path 41, and the introduction path 44 is sampled in the test tube 14 via the branch flow path 42.

Figure 4D:
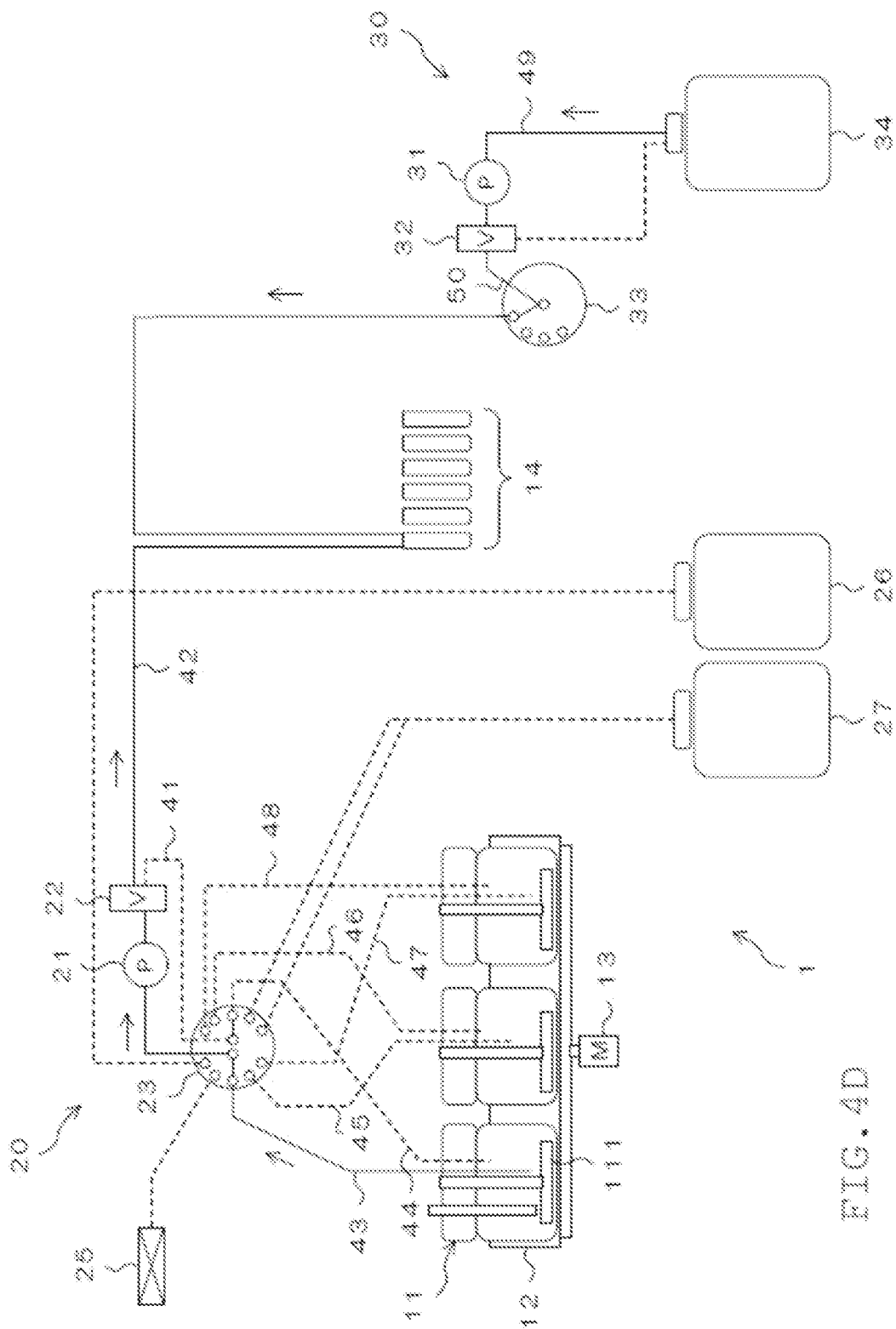
FIG. 4D is a flow path diagram for describing the operation of the sampling apparatus.

At this time, as illustrated in FIG. 4D, the valves 32 and 33 are also switched so that the flow path 49 communicates with the test tube 14 via the branch flow path 50. As a result, the reagent circulated in the flow path 49 can be sampled in the test tube 14 in which the culture medium is sampled.

Figure 4E:
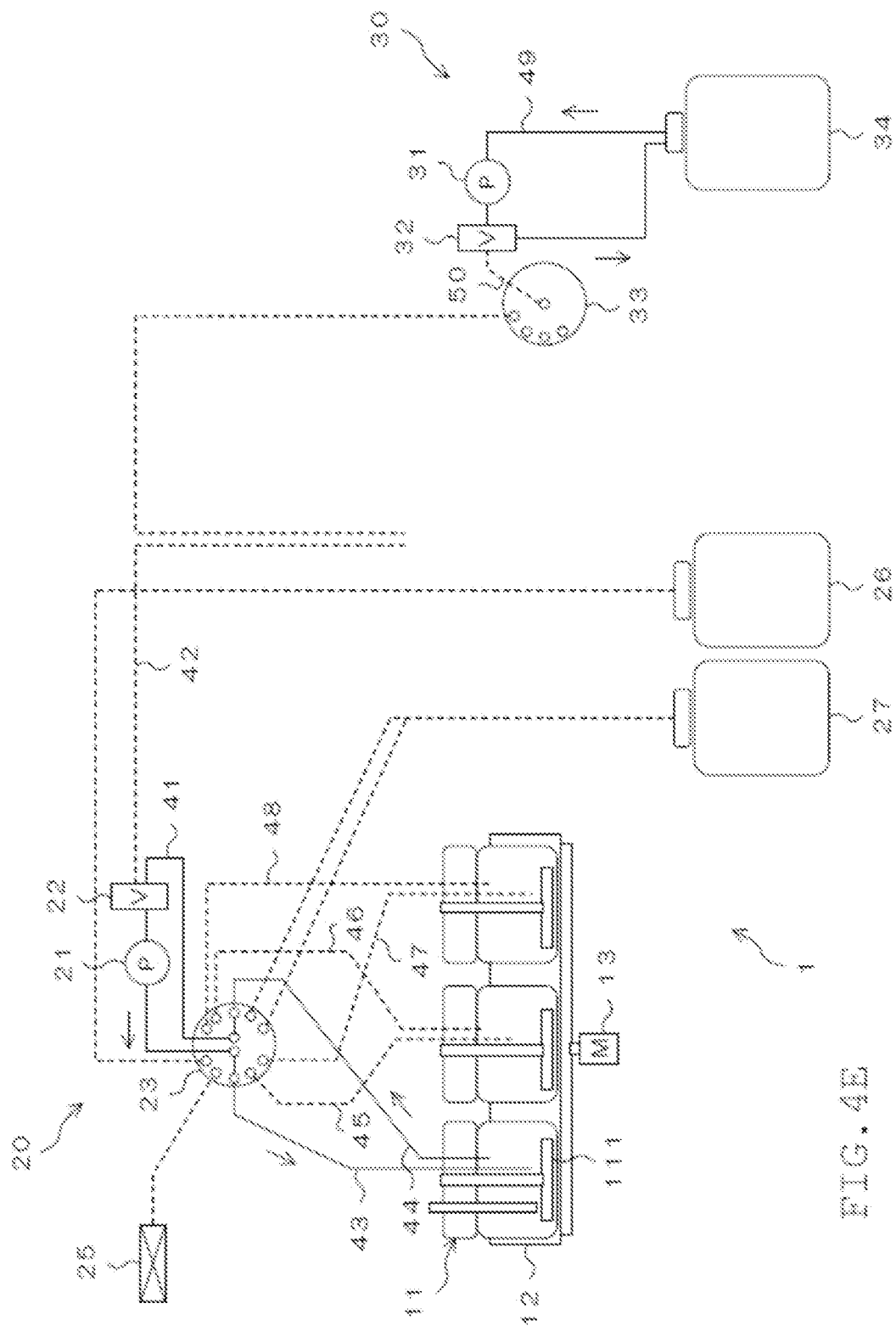
FIG. 4E is a flow path diagram for describing the operation of the sampling apparatus.

When the sampling of the culture medium and the reagent is completed, as illustrated in FIG. 4E, the valve 22 is switched to return to the state in which the lead-out path 43 and the introduction path 44 communicate with each other through the flow path 41. Further, the valve 32 is switched to return to the state in which the one end of the flow path 49 for the reagent communicates with the other end thereof. In this state, the pump 21 is driven to cause the liquid in the flow path 41 to flow back. As a result, the culture medium remaining in the flow path 41, the lead-out path 43, and the introduction path 44 flows back and is collected in the bioreactor 11.

Figure 4F:
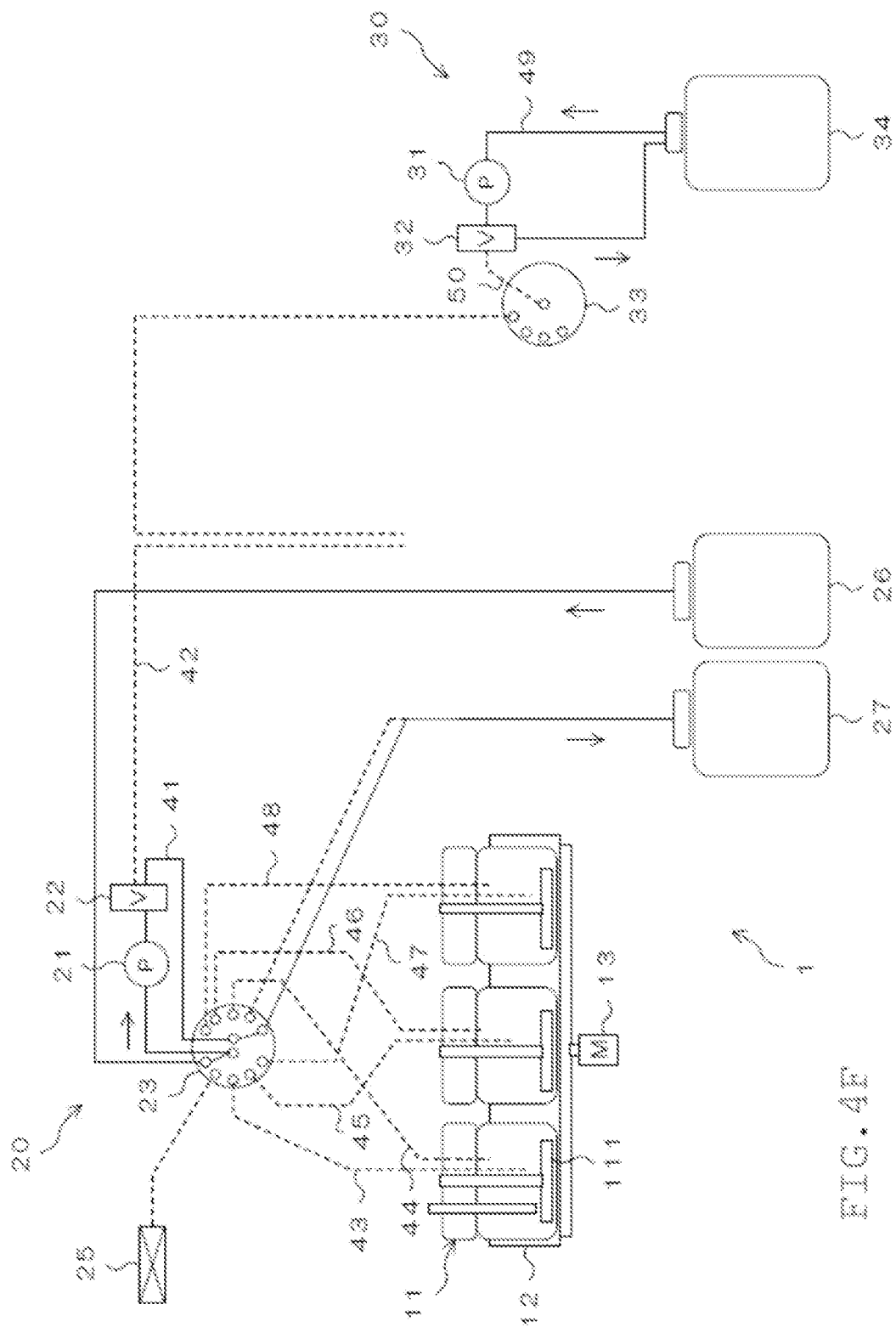
FIG. 4F is a flow path diagram for describing the operation of the sampling apparatus.

After that, as illustrated in FIG. 4F, the valve 23 is switched so that the cleaning liquid tank 26 and the waste liquid tank 27 communicate with each other via the flow path 41. When the pump 21 is driven in this state, the cleaning liquid in the cleaning liquid tank 26 is introduced into the flow path 41 and is drained into the waste liquid tank 27.

After that, as illustrated in FIG. 4G, the valve 23 is switched so that the filter 25 and the waste liquid tank 27 communicate with each other via the flow path 41. When the pump 21 is driven in this state, air is introduced into the flow path 41 via the filter 25, and is discharged to the waste liquid tank 27 together with the water remaining in the flow path 41.

5. Effects (1) In the present embodiment, with a simple configuration in which the flow path is only switched by using the valves 22 and 32 while the culture medium in the bioreactor 11 and the reagent in the reagent tank 34 are circulated in the flow paths 41 and 49, sampling can be performed by causing the liquid (culture medium or reagent) circulated in the flow paths 41 and 49 to flow out to the branch flow paths 42 and 50. When the flow paths are switched by the valves 22 and 32 for a predetermined time in a state where the liquid is stably circulated in the flow paths 41 and 49, an accurate amount of liquid according to the time can be sampled. In addition, sampling can be performed at high speed by repeating the switching of the flow paths by the valves 22 and 32 in a short time.

(2) In the present embodiment, the liquid (culture medium or reagent) can be sampled by using the pumps 21 and 31 with a simple configuration in which flexible tubes constituting at least a part of the flow paths 41 and 49 are deformed to feed the liquid. Further, when the inside of the tube becomes dirty or the like, maintenance can be performed easily and inexpensively simply by replacing the tube.

(3) In the present embodiment, the sampling amount of the liquid (culture medium or reagent) can be accurately controlled by accurately controlling the time for switching the flow paths by the valves 22 and 32, using the control unit 60.

(4) In the present embodiment, as illustrated in FIG. 4E, the culture medium remaining in the flow path 41 can be collected into the bioreactor 11 by causing the culture medium in the flow path 41 to flow back after the culture medium is sampled. Therefore, the amount of the culture medium used in the bioreactor 11 can be suppressed as compared with a case where the culture medium remaining in the flow path 41 is drained as it is.

(5) In the present embodiment, the culture medium remaining in the flow path 41 is collected into the bioreactor 11 after the culture medium is sampled, and then the inside of the flow path 41 can be cleaned with the cleaning liquid as illustrated in FIG. 4F. As a result, it is possible to reliably prevent the next sampling from being performed with the culture medium remaining in the flow path 41.

6. Modification Example

In the above embodiment, the case where the liquid sampled by the sampling apparatus 1 is a culture medium or a reagent has been described. However, without being limited to such a configuration, the sampling apparatus 1 according to the invention can be applied when any other liquid is sampled.

Further, the valves 22, 23, 32, and 33 are not limited to the configuration in which the valves 22, 23, 32, and 33 are automatically switched by the control unit 60, and may be configured to be manually switched by an operator. Similarly, the pumps 21 and 31 are not limited to the configuration in which the operation thereof is automatically started by the control unit 60, and may be configured such that the operation thereof is started based on an operation of the operator.

The circulation mechanism for circulating the liquid is not limited to the tubing pump such as the pumps 21 and 31 in the present embodiment, and the liquid can be circulated by using any other pump. Further, as long as the liquid can be circulated continuously and stably, without being limited to the configuration using the pump, a configuration using any other member may be adopted.

The sampling apparatus 1 is not limited to the configuration in which cells are cultured in the bioreactor 11 installed inside the sampling apparatus 1, and may be configured such that cells cultured externally are set in the sampling apparatus 1.

DESCRIPTION OF REFERENCE SIGNS 1 sampling apparatus
2 pre-processing apparatus
3 liquid chromatograph mass spectrometer
4 centrifugation mechanism
5 liquid removal mechanism
6 reagent supply mechanism
7 stirring mechanism
8 extraction mechanism
10 automatic pre-processing system
11 bioreactor
14 test tube
20 culture medium sampling mechanism
21 pump
22 valve
23 valve
25 filter
30 reagent sampling mechanism
31 pump
32 valve
33 valve
34 reagent tank
41 flow path
42 branch flow path
49 flow path
50 branch flow path

The invention claimed is:

1. A sampling apparatus that samples a liquid in a container, the sampling apparatus comprising:
a circulation mechanism that circulates the liquid in the container via a circulation flow path by leading out the liquid from the container into the circulation flow path and introducing the liquid from the circulation flow path into the container; and
a flow path switching unit that is provided in the middle of the circulation flow path, and switches a flow path such that the liquid circulated in the circulation flow path flows out to a branch flow path to be sampled,
a control unit that controls a sampling amount of the liquid by controlling time for switching the flow path by the flow path switching unit,
wherein the control unit collects the liquid into the container by causing the liquid in the circulation flow path to flow back after the liquid is sampled.

2. The sampling apparatus according to claim 1, wherein the circulation mechanism has a flexible tube constituting at least a part of the circulation flow path, and feeds the liquid in the tube by deforming the tube.

3. The sampling apparatus according to claim 1, wherein the control unit introduces a cleaning liquid into at least a part of the circulation flow path and drains the cleaning liquid after the liquid in the circulation flow path is collected into the container.

4. The sampling apparatus according to claim 1, wherein the liquid in the container is a culture medium containing cells.

\* \* \* \* \*